United States Patent [19]

Hauske et al.

[11] Patent Number: 4,518,590
[45] Date of Patent: May 21, 1985

[54] 9a-AZA-9a-HOMOERYTHROMYCIN COMPOUNDS, PHARMACEUTICAL COMPOSITIONS AND THERAPEUTIC METHOD

[75] Inventors: James R. Hauske, East Lyme; Arthur A. Nagel, Gales Ferry, both of Conn.

[73] Assignee: Pfizer Inc., New York, N.Y.

[21] Appl. No.: 616,529

[22] Filed: Jun. 4, 1984

Related U.S. Application Data

[63] Continuation-in-part of Ser. No. 600,252, Apr. 13, 1984.

[51] Int. Cl.$^3$ ................... A61K 31/70; C07H 17/08
[52] U.S. Cl. ................... 514/29; 536/7.2; 536/7.4
[58] Field of Search ........... 424/180; 536/7.2, 7.4

[56] References Cited

U.S. PATENT DOCUMENTS

| | | | |
|---|---|---|---|
| 4,150,220 | 4/1979 | Sciavolino | 536/9 |
| 4,180,654 | 12/1979 | Sciavolino | 536/9 |
| 4,328,334 | 5/1982 | Kobrehel et al. | 536/7.4 |
| 4,465,674 | 8/1984 | Bright et al. | 424/180 |

FOREIGN PATENT DOCUMENTS 2094293  9/1982  United Kingdom ........ 536/7.4

Primary Examiner—Johnnie R. Brown
Attorney, Agent, or Firm—Charles J. Knuth; Albert E. Frost; J. Trevor Lumb

[57] ABSTRACT

Certain novel 9-deoxo-4"-deoxy-4"-amino-9a-aza-9a-homoerythromycin A derivatives; a method of treating a bacterial infection in a mammalian subject using the novel erythromycin A derivatives; pharmaceutical compositions containing the novel erythromycin A derivatives; and intermediates and processes for making the novel erythromycin A derivatives.

23 Claims, No Drawings

9α-AZA-9α-HOMOERYTHROMYCIN COMPOUNDS, PHARMACEUTICAL COMPOSITIONS AND THERAPEUTIC METHOD

CROSS-REFERENCE TO RELATED APPLICATIONS

This application is a continuation-in-part of application Ser. No. 600,252, filed Apr. 13, 1984.

BACKGROUND OF THE INVENTION

This invention relates to novel chemical compounds which have antibacterial activity, and which are useful in the chemotherapy of bacterial infections in mammalian subjects. More particularly, the novel antibacterial agents of this invention are derivatives of the well-known macrolide antibiotic, erythromycin A, the compound of the following chemical structure:

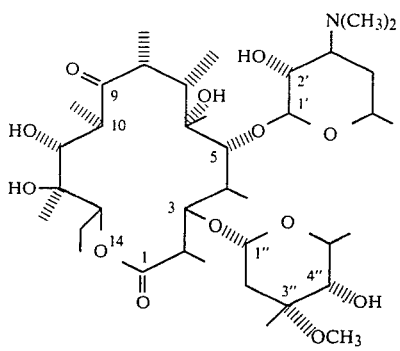

Even more particularly, the novel antibacterial agents of this invention are derivatives of erythromycin A, in which the 14-membered lactone ring has been expanded to a 15-membered ring by insertion of a nitrogen atom between ring-members 9 and 10, and the 4″-alpha-hydroxy group has been replaced by a substituent bonded to the 4″-position through a nitrogen atom (e.g. a primary amino group).

Thus the antibacterial agents of this invention can be regarded as derivatives of the compound of the formula II, viz.:

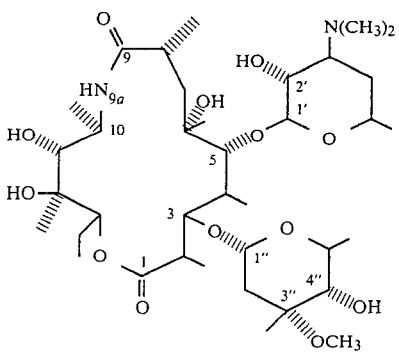

and for the purposes of this specification, the structure II is named chemically as 9a-aza-9a-homoerythromycin A, i.e. the locant 9a is used to identify the additional ring member in the lactone ring.

9a-Aza-9a-homoerythromycin A compounds have been disclosed in published British patent application No. 2,094,293 and U.S. Pat. No. 4,328,334, where they are named as 11-aza-10-deoxo-10-dihydroerythromycin A compounds. 4″-Deoxy-4″-amino-erythromycin A and 4″-deoxy-4″-acylamino-erythromycin A antibacterial agents are known from U.S. Pat. Nos. 4,150,220 and 4,180,654.

SUMMARY OF THE INVENTION

This invention provides novel macrolide antibiotics of the formula:

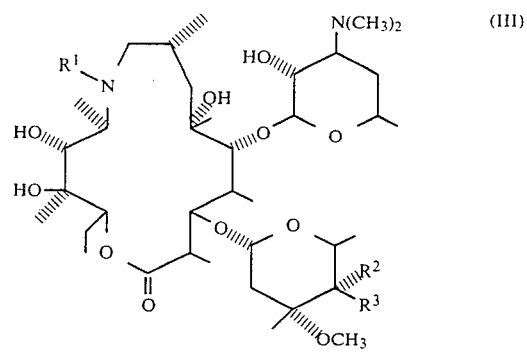

and the pharmaceutically-acceptable acid-addition salts thereof; wherein $R^1$ is selected from the group consisting of hydrogen and methyl; and $R^2$ and $R^3$ are each selected from the group consisting of hydrogen, amino and acylated-amino groups; provided that one of $R^2$ and $R^3$ is always hydrogen, but $R^2$ and $R^3$ are not both hydrogen.

Examples of acylated-amino groups are groups of the formulae NH—CO—$R^5$ and NH—SO$_2$—$R^6$, wherein:

(i) $R^5$ is selected from the group consisting of

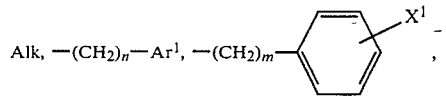

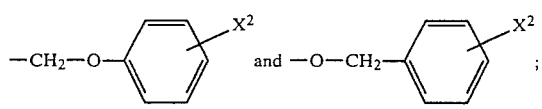

wherein

Alk is alkyl having from 1 to 8 carbons; $Ar^1$ is thienyl, furyl, isoxazolyl, pyridyl, pyrazinyl or pyrimidyl; $X^1$ is hydrogen, fluoro, chloro, bromo, hydroxy, amino, nitro, trifluoromethyl, alkyl having 1 to 3 carbons or alkoxy having 1 to 3 carbons; $X^2$ is hydrogen, fluoro, chloro or bromo; n is 0 or 1; and m is 0, 1, 2 or 3; and (ii) $R^6$ is selected from the group consisting of

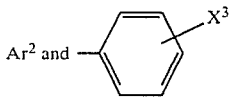

wherein $Ar^2$ is thienyl or furyl and $X^3$ is hydrogen, chloro, bromo or iodo.

Additionally, this invention provides a method of treating a bacterial infection in a mammalian subject, which comprises administering to said subject an antibacterially effective amount of a compound of formula III, wherein $R^1$, $R^2$ and $R^3$ are as defined above; and also pharmaceutical compositions containing a compound of formula III, wherein $R^1$, $R^2$ and $R^3$ are as defined above.

A first preferred group of compounds of this invention consists of the compounds of formula III, wherein $R^1$ is hydrogen or methyl, and either $R^2$ is hydrogen and $R^3$ is amino or $R^2$ is amino and $R^3$ is hydrogen.

A second preferred group of compounds of this invention consists of the compounds of formula III, wherein $R^1$ is methyl, $R^2$ is hydrogen and $R^3$ is NH—CO—$R^5$, wherein $R^5$ is

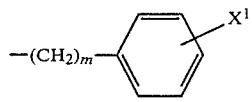

and m and $X^1$ are as defined previously.

A third preferred group of compounds of this invention consists of the compounds of formula III, wherein $R^1$ is methyl, $R^2$ is hydrogen and $R^3$ is NH—$SO_2$—$R^6$, wherein $R^6$ is

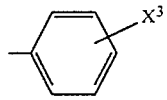

and $X^3$ is as defined previously.

Preferred individual compounds of the formula III are:

9-deoxo-9a-methyl-4''-deoxy-4''-alpha-amino-9a-aza-9a-homoerythromycin A (the compound of formula III, wherein $R^1$ is methyl, $R^2$ is amino and $R^3$ is hydrogen); and 9-deoxo-9a-methyl-4''-deoxy-4''-beta-amino-9a-aza-9a-homoerythromycin A (the compound of formula III, wherein $R^1$ is methyl, $R^2$ is hydrogen and $R^3$ is amino).

Yet further, this invention provides novel compounds of the formula:

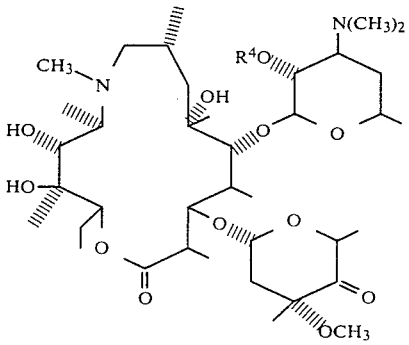

and the acid-addition salts thereof, wherein $R^4$ is selected from the group consisting of hydrogen, acetyl and propionyl. The compounds of formula IV are useful as intermediates to the antibacterial agents of formula III, wherein $R^1$ is methyl and $R^2$ and $R^3$ are as defined previously.

A particularly useful intermediate of the formula IV is 9-deoxo-9a-methyl-4''-deoxy-4''-oxo-9a-aza-9a-homoerythromycin A (the compound of formula IV, wherein $R^4$ is hydrogen).

DETAILED DESCRIPTION OF THE INVENTION

The antibacterial agents of this invention of formula III, wherein $R^1$ is hydrogen or methyl, and either $R^2$ is hydrogen and $R^3$ is amino or $R^2$ is amino and $R^3$ is hydrogen, can be prepared easily and conveniently from a 4''-deoxy-4''-aminoerythromycin A derivative of the formula V:

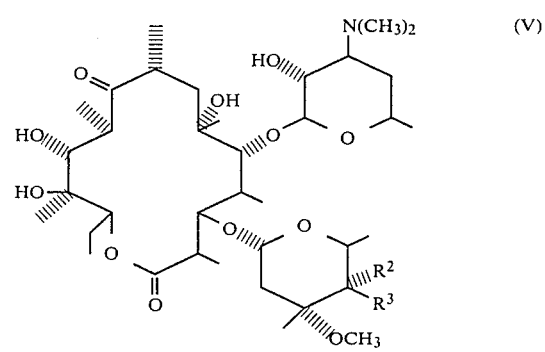

wherein either $R^2$ is hydrogen and $R^3$ is amino or $R^2$ is amino and $R^3$ is hydrogen. This is carried out according to Scheme A, in which only partial structures are shown.

SCHEME A

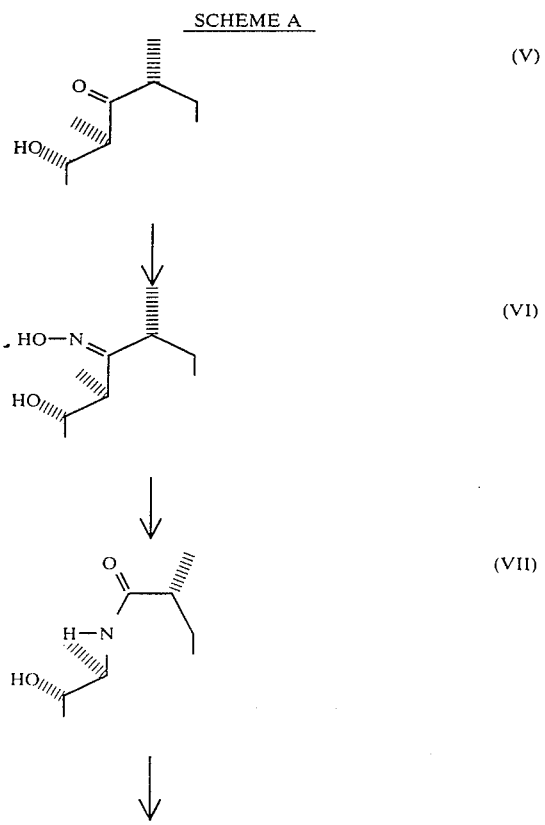

-continued
SCHEME A

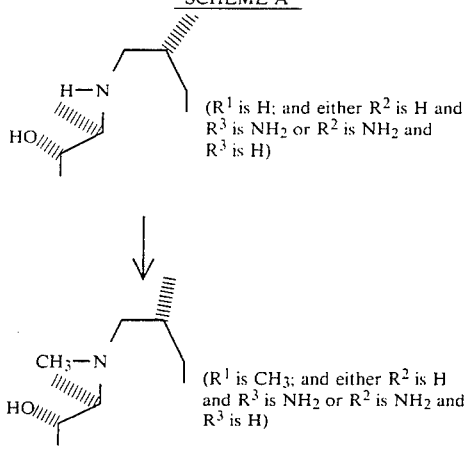

(III) (R¹ is H; and either R² is H and R³ is NH₂ or R² is NH₂ and R³ is H)

(III) (R¹ is CH₃; and either R² is H and R³ is NH₂ or R² is NH₂ and R³ is H)

In the first step of Scheme A, the 4"-deoxy-4"-aminoerythromycin A compound of formula V is converted into its oxime of formula VI. This is usually carried out by treating the compound of formula V with an excess of hydroxylamine, or an acid-addition salt thereof (e.g. the hydrochloride), in pyridine solution, at a temperature in the range from 20° to 60° C. The reaction usually takes several hours, e.g. about 15 to 50 hours, to reach completion, after which the product is isolated by diluting the reaction mixture with water, and extracting the product into a volatile, water-immiscible, organic solvent, such as ether or ethyl acetate. The product can then be recovered by drying the organic solvent, followed by evaporating the organic solvent in vacuo.

In the second step of Scheme A, the oxime of the formula VI is subjected to a Beckmann rearrangement to give the ring-expanded, 9a-aza-9a-homo-amide of the formula VII. This ring-expansion is conveniently carried out by treating the oxime of formula VI with an excess of 4-toluenesulfonyl chloride in the presence of a base at about room temperature. In one method, the oxime is added to aqueous acetone containing sodium bicarbonate, and then the 4-toluenesulfonyl chloride is added with the pH being maintained at about 8 by the addition of sodium hydroxide solution. Alternatively, the rearrangement can be carried out in a water-immiscible organic solvent, such as chloroform, in which case a slight excess of a tertiary amine is added to the oxime and the 4-toluenesulfonyl chloride. The rearrangement proceeds quite rapidly at ambient temperature, and in practice the reaction is allowed to proceed without external cooling. Under these conditions it is normally complete within 1 to 2 hours. When aqueous acetone has been used as the reaction solvent, the reaction mixture is diluted with water and the product is extracted into a volatile, water-immiscible organic solvent at a basic pH, followed by solvent evaporation. When a water-immiscible, organic solvent has been used for the Beckmann rearrangement, the product is extracted into an aqueous phase by extraction with water at an acidic pH. The water extract is then basified and the product is extracted into a volatile, water-immiscible organic solvent. Finally the water-immiscible, organic solvent is dried and evaporated in vacuo to give the desired 9a-aza-9a-homo-amide of the formula VII.

The compounds of the formula III, wherein R¹ is hydrogen, and either R² is hydrogen and R³ is amino or R² is amino and R³ is hydrogen, can be obtained by reduction of the 9,9a-amide grouping in the compound of formula VII. This can be carried out using a variety of agents known to reduce amides to amines, but in the present instance a particularly convenient reducing agent is sodium borohydride. When using sodium borohydride, a solution of the starting amide in a lower-alkanol, e.g. methanol, is treated with an excess of solid sodium borohydride, at a temperature from 0° to 30° C., and usually at about room temperature. At room temperature, the reaction proceeds quite smoothly and quickly, and it is normally complete within 1 to 2 hours. The reaction mixture can then be diluted with water and a volatile, water-immiscible, organic solvent, e.g. ethyl acetate. The pH is raised to about 10, and the organic layer is removed and dried. Evaporation of the organic layer then affords the desired compound of formula III.

The compounds of formula III, wherein R¹ is methyl, and either R² is hydrogen and R³ is amino or R² is amino and R³ is hydrogen, can be prepared by methylation at N-9a of the corresponding compound of formula III, wherein R¹ is hydrogen. However, before methylating at N-9a, it is preferable to protect the amino group at C-4", since the latter group is also susceptible to methylation. Thus, the preferred method of converting said compound of formula III, wherein R¹ is hydrogen, into the corresponding compound of formula III, wherein R¹ is methyl, involves protection of the amino group at C-4", followed by methylation at N-9a, followed by deprotection at C-4".

A variety of amino protecting groups can be used to protect the primary amino function at C-4", but particularly convenient groups are the benzyloxycarbonyl group and the 4-nitrobenzyloxycarbonyl group. These groups are attached to C-4" and they are removed from C-4" by standard methods, well-known in the art. For example, said compound of formula III is treated with a slight excess of benzyloxycarbonyl chloride or 4-nitrobenzyloxycarbonyl chloride in the presence of a tertiary amine, such as pyridine or triethylamine, at room temperature, in a reaction-inert organic solvent. The reaction proceeds quite rapidly, and it is usually complete within one hour. When a water-immiscible solvent, such as chloroform, has been used, the product is extracted into water at an acidic pH (e.g. pH 2) and then it is back-extracted into a volatile, water-immiscible, organic solvent at a basic pH (e.g. pH 10). Evaporation of the solvent then affords the C-4"-protected-amino compound. When a water-immiscible solvent has been used, the product can be isolated by diluting the reaction mixture with water and extracting with a volatile, water-immiscible organic solvent at a basic pH (e.g. pH 10). Evaporation of the solvent affords the product.

Methylation of the C-4"-protected-amino compound of the formula III, wherein R¹ is hydrogen, can be carried out conveniently using an excess of formaldehyde and formic acid in a reaction-inert organic solvent, such as chloroform. The reaction is usually carried out at a temperature from 60° to 100° C., and it usually takes a few hours, e.g. 2 to 6 hours, to reach completion. At the end of the reaction, the reaction mixture is cooled, and the C-4"-protected-amino compound of formula III, wherein R¹ is methyl, is isolated in exactly the same manner as described for isolation of the C-4" protected-amino compound of formula III, wherein R¹ is hydrogen.

The benzyloxycarbonyl or 4-nitrobenzyloxycarbonyl protecting group can be removed from the amino at C-4″ by hydrogenolysis in glacial acetic acid solution using palladium-on-carbon catalyst, according to standard procedures. The reaction is usually carried out at room temperature, and at a hydrogen pressure of from 1 to 10 kg/cm². The reaction is normally complete within a few hours, e.g. 4 to 10 hours. The catalyst is then removed by filtration and the acetic acid solution of the product is partitioned between water and a volatile, water-immiscible, organic solvent, such as ethyl acetate, at pH 8 to 10. The organic layer is removed, dried and evaporated to give the desired compound of formula III, wherein $R^1$ is methyl.

The novel 9a-aza-9a-homoerythromycin A derivatives of formula III, wherein $R^1$ is methyl, and either $R^2$ is hydrogen and $R^3$ is amino or $R^2$ is amino and $R^3$ is hydrogen, can also be prepared from the known 9a-aza-9a-homoerythromycin A derivative of the formula VIII:

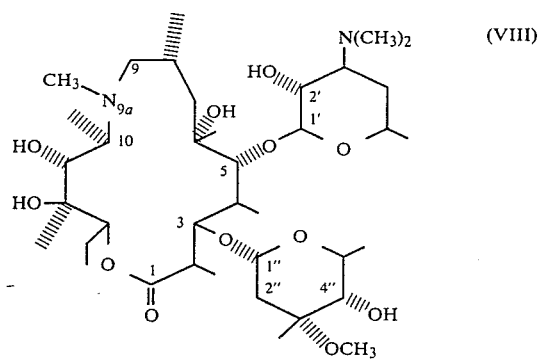

For preparation of the compounds of formula III, wherein $R^1$ is methyl, and either $R^2$ is hydrogen and $R^3$ is amino or $R^2$ is amino and $R^3$ is hydrogen, the compound of formula VIII is first converted into the corresponding 4″-keto compound of the formula IX:

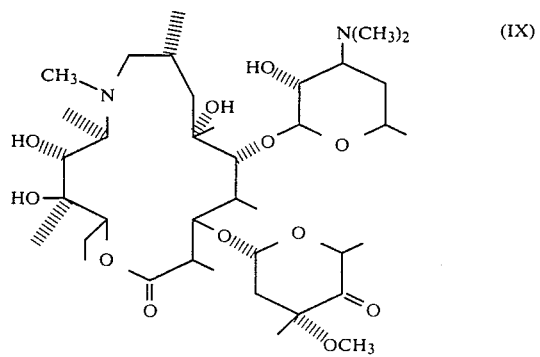

Conversion of the compound of the formula VIII into the compound of the formula IX involves protection of the 2′-hydroxy group, followed by oxidation of the 4″-hydroxy group to a keto group, followed by removal of the protecting group from the 2′-hydroxy group.

Protection of the 2′-hydroxy group is usually achieved using a lower-alkanoyl protecting group, e.g. acetyl or propionyl. The acetyl or propionyl group is attached to the 2′-hydroxy group by treatment of the compound of formula VIII with a slight excess of acetic anhydride or propionic anhydride in chloroform, at room temperature, for several hours, according to standard procedures. Oxidation to the corresponding 2′-O-acetyl-4″-deoxy-4″-keto compound (or its 2′-O-propionyl analog) is then achieved by treatment with dimethyl sulfoxide and a carbodiimide in the presence of a base. N-Ethyl-N′-(N,N-dimethylaminopropyl)carbodiimide is conveniently used as the carbodiimide and pyridinium trifluoroacetate is conveniently used as the base. Finally, removal of the 2′-O-acetyl or 2′-O-propionyl group can be achieved by solvolysis with methanol at 10° to 30° C. for 1 to 2 days, followed by removal of the methanol by evaporation in vacuo.

For preparation of the compound of the formula III, wherein $R^1$ is methyl, $R^2$ is amino and $R^3$ is hydrogen, the compound of formula IX is converted into its C-4″ oxime, and then the oxime is reduced with gaseous hydrogen over a Raney nickel catalyst.

The oxime is prepared by treating the ketone (IX) with an excess of hydroxylamine hydrochloride in methanol solution at room temperature for several hours. It is then isolated by removal of the solvent in vacuo. Reduction of the C-4″ oxime of the compound of the formula IX is achieved by treatment with hydrogen, at room temperature, over a Raney nickel catalyst, in a solvent such as a lower-alkanol (e.g. ethanol) and at a pressure in the range from 1 to 10 kg/cm², and preferably 4 to 5 kg/cm². The catalyst is removed by filtration and the product can then be recovered by solvent evaporation.

For preparation of the compound of formula III, wherein $R^1$ is methyl, $R^2$ is hydrogen and $R^3$ is amino, the compound of formula IX can be reductively aminated. This can be achieved by contacting the compound of formula IX with an excess of ammonium acetate, in a lower-alkanol, such as methanol, and then reducing the resulting adduct with sodium cyanoborohydride. In practice this produces the compound of formula III, wherein $R^1$ is methyl, $R^2$ is hydrogen and $R^3$ is amino, together with its C-4″-epimer. Also, some of the corresponding C-4″-hydroxy compounds (compound VIII and its C-4″-epimer) are formed. The C-4″-hydroxy compounds are readily removed during work-up. The total reaction product is partitioned between ethyl acetate and water at pH 6, under which conditions the C-4″-hydroxy compounds are extracted into the organic layer while the C-4″-amino compounds remain in the aqueous layer. At this point, the ethyl acetate layer is separated and discarded, and the pH of the aqueous layer is raised to 9 to 10. The C-4″-amino compounds can then be extracted into an organic phase, which is then separated, dried and evaporated in vacuo. The compound of formula III, wherein $R^1$ is methyl, $R^2$ is hydrogen and $R^3$ is amino, can be separated from its C-4″-epimer by chromatography.

The antibacterial agents of this invention of the formula III, wherein $R^1$ is hydrogen or methyl, and either $R^2$ is hydrogen and $R^3$ is acylated-amino or $R^2$ is acylated-amino and $R^3$ is hydrogen, are prepared from the corresponding compound of formula III, wherein $R^1$ is hydrogen or methyl, and either $R^2$ is hydrogen and $R^3$ is amino or $R^2$ is amino and $R^3$ is hydrogen. This latter process involves, therefore, acylation of $R^2$ or $R^3$ as amino to $R^2$ or $R^3$ as $NH-CO-R^5$ or $NH-SO_2-R^6$, wherein $R^5$ and $R^6$ are as defined previously.

Acylation of $R^2$ or $R^3$ as amino can be carried out using standard techniques. For example, the appropriate compound of formula III, wherein $R^2$ or $R^3$ is amino, can by acylated by treatment with an activated derivative, such as an acid chloride, of the appropriate acid of the formula $R^5$—CO—OH or $R^6$—$SO_2$—OH. The reaction is usually carried out by contacting the compound of formula III, wherein $R^2$ or $R^3$ is amino, with one molar equivalent or a small excess (i.e. from 1.0 to 1.3 molar equivalents) of the activated derivative of the acid of the formula $R^5$—CO—OH or $R^6$—$SO_2$—OH in a reaction-inert solvent at a temperature in the range from 0° to 40° C. and preferably 20° to 25° C. Typical solvents which can be used include: chlorinated hydrocarbons, such as dichloromethane and chloroform; low-molecular weight ethers, such as diethyl ether, tetrahydrofuran and dioxane; low-molecular weight ketones, such as acetone and methyl isobutyl ketone; low-molecular weight esters, such as ethyl acetate; and mixtures thereof. Moreover, when an acid chloride is used as the activated derivative, it is often convenient to add one molar equivalent of an acid-binder such as triethylamine, pyridine or N,N-dimethylaniline. The reaction proceeds quite rapidly, and it is normally complete within a short time, e.g. 0.5 to 24 hours. At the end of the reaction, the reaction mixture is usually partitioned between a water-immiscible, organic solvent and water, at a pH between 2 and 4. The organic layer is then removed and discarded, and the pH of the aqueous phase is raised to a value from 6.5 to 10, and the product is extracted into a volatile, water-immiscible, organic solvent. The organic solvent is then dried and evaporated to give the acylated product (III; $R^2$ or $R^3$ is NH—CO—$R^5$ or NH—$SO_2$—$R^6$).

Alternatively, for conversion of $R^2$ or $R^3$ as amino into $R^2$ or $R^3$ as NH—CO—$R^5$, the acid of formula $R^5$—CO—OH can be activated by conversion into a mixed anhydride. In this case, a carboxylate salt of the acid of the formula $R^5$—CO—OH is reacted with one equivalent of a lower-alkyl chloroformate at a temperature from −40° to 0° C., and preferably about −15° C. Typical carboxylate salts are amine salts such as triethylamine or N-methylmorpholine salts, and the mixed anhydride is usually prepared in the same solvent that is to be used for the acylation reaction, and it is usually used without isolation.

Yet further, for conversion of $R^2$ or $R^3$ as amino into $R^2$ or $R^3$ as NH—CO—$R^5$, the carboxylic acid of the formula $R^5$—CO—OH can be activated by contacting it with certain agents known in the art for forming peptide bonds. Such agents include carbodiimides, such as dicyclohexylcarbodiimide, ethoxyacetylene and N-ethoxycarbonyl-2-ethoxy-1,2-dihydroquinoline.

Thus, the compounds of formula III, wherein $R^1$ is methyl, and either $R^2$ is hydrogen and $R^3$ is acylated-amino or $R^2$ is acylated-amino and $R^3$ is hydrogen, can be prepared by acylation of the corresponding compound of formula III, wherein $R^1$ is methyl, and either $R^2$ is hydrogen and $R^3$ is amino or $R^2$ is amino and $R^3$ is hydrogen. However, the compounds of formula III, wherein $R^1$ is methyl, and either $R^2$ is hydrogen and $R^3$ is acylated-amino or $R^2$ is acylated-amino and $R^3$ is hydrogen, can also be prepared by methylation of the corresponding compound wherein $R^1$ is hydrogen. This methylation is carried out using an excess of formaldehyde and formic acid, in an inert solvent, as described previously for methylation at N-9a.

The antibacterial agents of this invention of formula III, and the intermediate compounds of formulae IV, V, VI, VII and IX, can all be purified after preparation, if desired, by standard procedures for macrolide compounds. Such procedures include recrystallization, column chromatography, preparative thin-layer chromatography and counter-current distribution.

The antibacterial compounds of the formula III, and the intermediates of formula IV, are basic and therefore they will form acid-addition salts. All such salts are within the scope of this invention, and they can be prepared by standard procedures for macrolide compounds. The compounds of formula III and IV contain more than one basic center, and mono-, di- or tri-acid-addition salts can be prepared. For di- and tri-acid-addition salts the anionic counter ions can be the same or different. In general, for preparation of the acid-addition salts, the compound of formula III or IV is combined with a stoichiometric amount of an appropriate acid in an inert solvent, and then the salt is recovered by solvent evaporation, by filtration if the salt precipitates spontaneously, or by precipitation using a non-solvent followed by filtration. Typical salts which can be prepared include sulfate, hydrochloride, hydrobromide, nitrate, phosphate, citrate, tartrate, pamoate, sulfosalicylate, methanesulfonate, benzenesulfonate and 4-toluenesulfonate salts.

The starting materials of formula V, wherein either $R^2$ is hydrogen and $R^3$ amino or $R^2$ is amino and $R^3$ is hydrogen, can be prepared by reductive amination of 4″-deoxy-4″-oxo-erythromycin A, the compound of the formula X:

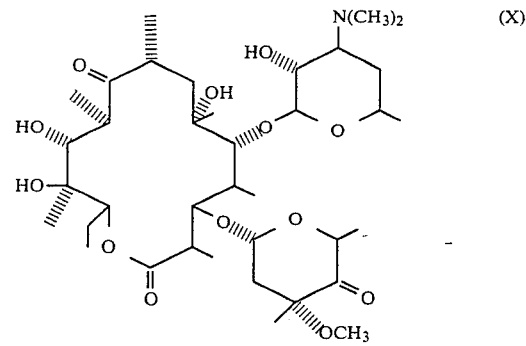

In order to prepare the compound of formula V, wherein $R^2$ is hydrogen and $R^3$ is amino, a mixture of the compound of formula X and an excess of ammonium acetate in methanol is hydrogenated at ambient temperature, at a pressure of about 4 kg/cm$^2$, in the presence of 10% palladium-on-carbon catalyst. This affords predominantly the C-4″-beta-amino compound, which can be obtained pure by trituration under ether.

The compound of formula V, wherein $R^2$ in amino and $R^3$ is hydrogen, can be prepared by hydrogenation of a mixture of the compound of formula X and an excess of ammonium acetate in methanol, at ambient temperature, at a hydrogen pressure of ca. 4 kg/cm$^2$, using a Raney nickel catalyst. This affords predominantly the C-4″-alpha-amino compound, which can be obtained pure by repeated recrystallization from a solvent such as isopropanol.

4″-Deoxy-4″-oxo-erythromycin A, the compound of formula X, can be prepared according to the procedures described in U.S. Pat. No. 4,150,220.

9-Deoxo-9a-methyl-9a-aza-9a-homoerythromycin A, the compound of formula VIII, can be prepared according to the procedure of published British patent application No. 2,094,293. See further Example 1 of said GB No. 2,094,293, wherein the compound of formula VIII is named N-methyl-11-aza-10-deoxo-10-dihydro-erythromycin A. See also U.S. Pat. No. 4,328,344 and West German Offenlegungsschrift DE-OS No. 3012533.

The compounds of formula III, wherein $R^1$ is hydrogen or methyl, and $R^2$ and $R^3$ are hydrogen, amino, NH—CO—$R^5$ or NH—SO$_2$—$R^6$, provided that one of $R^2$ and $R^3$ is hydrogen but $R^2$ and $R^3$ are not both hydrogen, are useful as antibacterial agents both in vitro and in vivo, and their spectrum of activity if similar to that of erythromycin A. Consequently, they can be used for the same purposes, and in the same manner, as erythromycin A. In general, the antibacterial compounds of formula III and salts thereof, exhibit in vitro activity against a variety of Gram-positive microorganisms, e.g., *Staphylococcus aureus* and *Streptococcus pyogenes,* and against certain Gram-negative microorganisms such as those of spherical or ellipsodial shape (cocci). Their activity is readily demonstrated by in vitro tests against various micro-organisms in a brain-heart infusion medium by the usual two-fold serial dilution technique. Their in vitro activity renders them useful for topical application; for sterilization purposes, e.g., sick-room utensils; and as industrial antimicrobials, for example, in water treatment, slime control, paint and wood preservation. For in vitro use for topical application, it will usually be convenient to prepare pharmaceutical compositions, in which the compound of formula III is combined with a pharmaceutically-acceptable carrier or diluent, for example in the form of ointments and creams. Appropriate carriers and diluents for these purposes include mineral oils and vegetable oils, and solvents such as water, alcohols, and glycols, and mixtures thereof. Such a pharmaceutical composition will normally contain the pharmaceutically-acceptable carrier and the compound of formula III in a weight ratio in the range from 4:1 to 1:4.

Additionally the antibacterial compounds of formula III, and the pharmaceutically-acceptable salts thereof, are active in vivo versus a variety of Gram-positive microorganisms, e.g. *Staphylococcus aureus* and *Streptococcus pyogenes,* and also certain Gram-negative microorganisms, via the oral and parenteral routes of administration, in animals, including man. Their in vivo activity is more limited than their in vitro activity as regards susceptible organisms, and it is determined by the usual procedure which comprises infecting mice of substantially uniform weight with the test organism and subsequently treating them orally or subcutaneously with the test compound. In practice, the mice, e.g., 10, are given an intraperitoneal inoculation of suitable diluted cultures containing approximately 1 to 10 times the LD$_{100}$ (the lowest concentration of organisms required to produce 100% deaths). Control tests are simultaneously run in which mice receive inocula of lower dilutions as a check on possible variation in virulence of the test organism. The test compound is administered 0.5 hour post-inoculation, and is repeated 4, 24 and 48 hours later. Surviving mice are held for four days after the last treatment and the number of survivors is noted.

When used in vivo to treat a bacterial infection in a mammalian subject, especially man, the compounds of formula III and salts thereof can be administered alone, or, preferably, in the form of pharmaceutical compositions containing a pharmaceutically-acceptable carrier or diluent. Such compositions can be administered orally, for example as tablets or capsules, or parenterally, which includes subcutaneous and intramuscular injection. The pharmaceutically-acceptable carrier will depend on the intended mode of administration. For example, lactose, sodium citrate and salts of phosphoric acid, together with disintegrating agents (such as starch) and lubricating agents (such as magnesium stearate, sodium lauryl sulfate and talc) can be used as the pharmaceutically-acceptable carrier in tablets. Also, for use in capsules useful pharmaceutically-acceptable carriers are lactose and high molecular weight polyethylene glycols (e.g., having molecular weights from 2,000 to 4,000). For parenteral use, sterile solutions or suspensions can be prepared, wherein the pharmaceutically-acceptable carrier is aqueous (e.g., water, isotonic saline or isotonic dextrose) or non-aqueous (e.g., fatty oils of vegetable origin such as cottonseed or peanut oil, or polyols such as glycerol or propylene glycol).

For in vivo use of a compound of the formula III, or a salt thereof, a pharmaceutical composition will usually contain the pharmaceutically-acceptable carrier and the compound of formula III or salt thereof in a weight ratio in the range from 4:1 to 1:4.

When used in vivo to treat a bacterial infection in a mammalian subject, either orally or parenterally, the usual daily dosage of an antibacterial compound of the formula III, or a salt thereof, will be in the range from 5 to 100 mg/kg of body weight, especially 10 to 50 mg/kg of body weight, in single or divided doses.

The following examples and preparations are being provided solely for the purpose of additional illustration. Proton nuclear magnetic resonance spectra ($^1$H-NMR spectra) were measured as solutions in deuterated chloroform (CDCl$_3$), and peak positions of diagnostic absorptions are reported in parts per million (ppm) downfield from internal tetramethylsilane. The following abbreviations for peak shapes are used: s, singlet; bs, broad singlet; d, doublet; m, multiplet.

EXAMPLE 1

9-Deoxo-9a-methyl-4"-deoxy-4"-beta-amino-9a-aza-9a-homoerythromycin A

A.

9-Deoxo-4"-deoxy-4"-beta-benzyloxycarbonylamino-9a-aza-9a-homoerythromycin A

To a stirred solution of 0.5 g (0.68 mmole) of 9-deoxo-4"-deoxy-4"-beta-amino-9a-aza-9a-homoerythromycin A and 0.11 ml (1.0 mmole) of pyridine in 20 ml of dichloromethane was added a solution of 0.15 ml (1.0 mmole) of benzyloxycarbonyl chloride (benzyl chloroformate) in 5 ml of dichloromethane. The reaction mixture was stirred at room temperature for 30 minutes, and then an excess of water was added. The pH of the aqueous phase was adjusted to 2, and the organic layer was removed and discarded. The pH of the aqueous layer was raised to 5, and then the aqueous layer was extracted with chloroform and the chloroform extracts were discarded. The pH of the aqueous layer was then raised to 8 and the aqueous layer was again extracted with chloroform. The latter chloroform extracts were washed with water, dried, and evaporated in vacuo to give 0.43 g of the 4"-beta-benzyloxycarbonylamino derivative.

B.

9-Deoxo-9a-methyl-4"-deoxy-4"-beta-benzyloxycarbonylamino-9a-aza-9a-homoerythromycin A A mixture of the product of Part A (0.43 g), 0.2 ml of 37% aqueous formaldehyde, 0.05 ml of 98% formic acid and 30 ml of chloroform was heated under reflux for 3.5 hours. The reaction mixture was then cooled and diluted with an excess of water. The pH was adjusted to 9, and the mixture was extracted with chloroform. The chloroform extracts were washed with water, dried, and evaporated in vacuo to give 0.40 g of the 9a-methyl derivative.

C.
9-Deoxo-9a-methyl-4″-deoxy-4″-beta-amino-9a-aza-9a-homoerythromycin A

The product of Part B (0.40 g) was dissolved in 5 ml of glacial acetic acid, and then 100 mg of 10% palladium-on-carbon was added, under nitrogen. The resulting mixture was shaken under an atmosphere of hydrogen for 5.5 hours at a pressure of ca. 4 kg/cm$^2$, and then the catalyst was removed by filtration. To the filtrate was added ethyl acetate and water and the pH of the aqueous phase was adjusted to 9.5. The ethyl acetate layer was removed, and the aqueous layer was extracted with further ethyl acetate. The ethyl acetate solutions were combined, washed with water and dried. Evaporation of the dried solution gave 0.04 g of 9-deoxy-9a-methyl-4″-deoxy-4″-beta-amino-9a-aza-9a-homoerythromycin A.

The $^1$H-NMR spectrum of the product showed absorptions at 2.13 (broad singlet, 9H) and 3.28 (singlet, 3H) ppm.

EXAMPLE 2

9-Deoxo-9a-methyl-4″-deoxy-4″-alpha-amino-9a-aza-9a-homoerythromycin A

The title compound can be prepared from 9-deoxo-4″-deoxy-4″-alpha-amino-9a-aza-9a-homoerythromycin A by reaction with benzyloxycarbonyl chloride, followed by reaction with formaldehyde-formic acid, followed by hydrogenolysis, using the procedures of Parts A, B and C of Example 1.

EXAMPLE 3

9-Deoxo-4″-deoxy-4″-alpha-amino-9a-aza-9a-homoerythromycin A

A. 4″-Deoxy-4″-alpha-amino-erythromycin A oxime

A mixture of 6.4 g (8.6 mmole) of 4″-deoxy-4″-alpha-amino-erythromycin A, 3.2 g (46 mmole) of hydroxylamine hydrochloride and 65 ml of pyridine was heated to 50° C., and maintained at that temperature for ca. 18 hours. The reaction mixture was then added to a mixture of diethyl ether and water, and the pH of the aqueous layer was adjusted to 10. The layers were separated, and the aqueous layer was extracted further wtih ether. The combined ether solutions were washed with water, followed by saturated sodium chloride solution, and then the ether solution was dried (Na$_2$SO$_4$). Evaporation of the ether solution gave a foam. To the foam was added more ether, and the mixture was heated on a steam bath and then allowed to cool. The solid material was filtered off to give a first crop (3.86 g) of the required oxime. The ether filtrate was evaporated in vacuo to give a second crop (1.9 g) of the required oxime.

B.
4″-Deoxy-4″-alpha-amino-9a-aza-9a-homoerythromycin A

To a solution of the second crop of the oxime of Part A (1.9 g; 2.5 mmole) in a mixture of 40 ml of acetone and 30 ml of water was added 1.5 g (18 mmole) of sodium bicarbonate, and then the mixture was cooled to ice-bath temperature. To the resulting mixture was added a solution of 1.0 g (5.0 mmole) of 4-toluenesulfonyl chloride in ca. 10 ml of acetone, dropwise with stirring during 10 minutes. During the addition, aqueous sodium hydroxide was added as needed to keep the pH at approximately 8. Stirring was continued for 30 minutes, and then the reaction mixture was poured into a mixture of water and dichloromethane. The pH of the aqueous layer was adjusted to 5 and the dichloromethane layer was removed. The aqueous residue was then extracted with dichloromethane at pH 6.0, 6.5 and 10. The dichloromethane solution from the extraction at pH 10 was evaporated in vacuo and the residue recrystallized from ether, to give a first crop of the desired 9a-aza-9a-homo compound. The dichloromethane solution from the extraction at pH 6.5 was evaporated in vacuo to give a second crop of the desired 9a-aza-9a-homo compound. The mother liquor from the ether recrystallization was evaporated in vacuo to give a third crop of the desired 9a-aza-9a-homo compound. The three crops were combined to give 1.0 g of the desired 9a-aza-9a-homo compound.

C.
9-Deoxo-4″-deoxy-4″-alpha-amino-9a-aza-9-homoerythromycin A

A solution of the product of Part B (1.0 g; 1.3 mmole) in 40 ml of methanol was cooled to ice-bath temperature, and then 2.0 g of sodium borohydride was added portionwise, with stirring. Stirring was continued for 1 hour, and then the reaction mixture was diluted with water and ethyl acetate. The pH was adjusted to 9, and the ethyl acetate layer was removed, washed with water, and dried. Evaporation of the ethyl acetate solution afforded 500 mg of the 9a-deoxo-9a-aza-9a-homo compound.

The latter 9a-deoxo-9a-aza-9a-homo compound was combined with an additional 1.28 g of material of similar quality prepared in an analogous fashion, and the mixture was purified by column chromatography on silica gel, using chloroform/methanol/ammonium hydroxide (9:5:0.05) as eluant. Evaporation of the appropriate fractions gave 600 mg of 9-deoxo-4″-deoxy-4″-alpha-amino-9a-aza-9a-homoerythromycin A.

The $^1$H-NMR spectrum of the product showed absorptions at 2.29 (singlet, 6H) and 3.33 (singlet, 3H) ppm.

EXAMPLE 4

9-Deoxo-4″-deoxy-4″-beta-amino-9a-aza-9a-homoerythromycin A

A. 4″-Deoxy-4″-beta-aminoerythromycin A oxime

A mixture of 50 g (68 mmole) of 4″-deoxy-4″-beta-aminoerythromycin A, 25 g (360 mmole) of hydroxylamine hydrochloride and 250 ml of pyridine was stirred at room temperature for 2 days. To the reaction mixture was then added water and ethyl acetate and the pH was adjusted to 10. The ethyl acetate layer was removed, dried, and evaporated in vacuo to give a foam. The foam was recrystallized from ether to give 14 g of the desired oxime. The mother liquor was evaporated in vacuo to give a foam, which was triturated under petroleum ether and then recrystallized from ether to give an additional 6.0 g of the desired oxime.

Evaporated of the mother liquor from the second recrystallization, and treatment of the residue with 15 g of hydroxylamine hydrochloride in 60 ml of pyridine as above, afforded a further 4.5 g of the desired oxime.

B.
4"-Deoxy-4"-beta-amino-9a-aza-9a-homoerythromycin A

A mixture was prepared from 14.0 g (18.7 mmole) of 4"-deoxy-4"-beta-aminoerythromycin A from Part A, 5.3 g (28 mmole) of 4-toluenesulfonyl chloride, 4.2 ml (30 mmole) of triethylamine and 100 ml of chloroform, with stirring. The temperature rose to 33° C., and then the reaction mixture was cooled to room temperature with ice-bath cooling. The reaction mixture was stirred at room temperature for 1 hour, and then an excess of water was added. The pH of the aqueous phase was adjusted to 5 using 1N hydrochloric acid and the layers were separated. The pH of the aqueous layer was adjusted to 10, and then it was extracted with ethyl acetate. The ethyl acetate extracts were dried and evaporated in vacuo. The residue was recrystallized from ether to give 7.0 g of the desired 9a-aza-9a-homo compound.

C.
9-Deoxo-4"-deoxy-4"-beta-amino-9a-aza-9a-homoerythromycin A

The 4"-deoxy-4"-beta-amino-9a-aza-9a-homoerythromycin A from Step B (7.0 g; 9.4 mmole) was dissolved in 300 ml of methanol and cooled to 10°–15° C. in an ice-bath. To this solution was then added 7.5 g (0.2 mole) of sodium borohydride portionwise with stirring, during about 20 minutes. Stirring was continued for 3 hours and then an excess of water was added. The resulting mixture was extracted several times with chloroform and the extracts were dried and evaporated in vacuo. The residue (9.0 g) was dissolved in a mixture of 100 ml of acetate and 50 ml of water, and 9.0 g (55 mmole) of mannitol was added, followed by 1.7 g (20 mmole) of sodium bicarbonate. The resulting mixture was stirred at room temperature for 18 hours, and then it was diluted with water and extracted with ethyl acetate. The ethyl acetate solution was dried and evaporated to give 1.5 g of a first crop of the desired 9-deoxo-9a-aza-9a-homo compound.

The residual aqueous phase from the ethyl acetate extraction was further extracted with chloroform, and the chloroform solution was dried and evaporated to give 4.5 g of residue. The residue was dissolved in 300 ml of chloroform, and 150 g of silica gel was added. The mixture was stirred at room temperature for 18 hours, and then it was filtered. The silica gel was washed with 300 ml of chloroform, followed by 500 ml of chloroform/methanol/ammonium hydroxide (100:1:0.1), followed by 500 ml of chloroform/methanol/ammonium hydroxide (4:1:0.1). The original filtrate, after removal of the silica gel, and all of the silica gel washings were combined and evaporated in vacuo. The residue was combined with the first crop of the desired 9-deoxo-9a-aza-9a-homo compound from above and added to 100 ml of water. The pH was adjusted to 5 and the mixture was stirred at pH 5 for 25 minutes. The pH was raised to 10, and the aqueous phase was extracted with dichloromethane. The dichloromethane extracts were dried and evaporated in vacuo to give 4.3 g of 9-deoxo-4"-deoxy-4"-beta-amino-9a-aza-9a-homoerythromycin A.

The $^1$H-NMR spectrum of the product showed absorptions at 2.24 (singlet, 6H) and 3.28 (singlet, 3H) ppm.

EXAMPLE 5
9-Deoxo-9a-methyl-4"-deoxy-4"-alpha-amino-9a-aza-9a-homoerythromycin A A.
9-Deoxo-9a-methyl-4"-deoxy-4"-oxo-9a-aza-9a-homoerythromycin A oxime A solution of 7.5 g (9.5 mmole) of 9-deoxo-9a-methyl-2'-O-acetyl-4"-deoxy-4"-oxo-9a-aza-9a-homoerythromycin A in 50 ml of methnal was stored at room temperature for 2 days, and then 3.5 g (50 mmole) of hydroxylamine hydrochloride was added. The resulting mixture was stirred at room temperature for 3 hours and then the solvent was removed by evaporation in vacuo. The residue was partitioned between ethyl acetate and water, and the pH of the aqueous phase was raised to 9. The layers were separated and the organic layer was dried and evaporated in vacuo. The residue was recrystallized from ether to give 4.4 g of the desired oxime.

B.
9-Deoxo-9a-methyl-4"-deoxy-4"-alpha-amino-9a-aza-9a-homoerythromycin A

A mixture of 4.4 g (5.8 mmole) of the oxime from Part A and ca. 4 g of Raney nickel in 100 ml of ethanol was shaken under an atmosphere of hydrogen at a pressure of 4.5 kg/cm$^2$ for ca. 75 hours. The mixture was then filtered, and the filtrate was evaporated in vacuo to give a foam. The foam was dissolved in diisopropyl ether, and the solvent was allowed to evaporate slowly. After 24 hours, the white solid which had precipitated was collected to give 2.2 g of 9-deoxo-9a-methyl-4"-deoxy-4"-alpha-amino-9a-aza-9a-homoerythromycin A.

The $^1$H-NMR spectrum of the product showed absorptions at 2.31 (singlet, 6H), 2.35 (singlet, 3H) and 3.31 (singlet, 3H) ppm.

EXAMPLE 6
9-Deoxo-9a-methyl-4"-deoxy-4"-beta-amino-9a-aza-9a-homoerythromycin A

A.
9-Deoxo-9a-methyl-4"-deoxy-4"-oxo-9a-aza-9a-homoerythromycin A

A solution of 0.93 g (1.2 mmole) of 9-deoxo-9a-methyl-2'-O-acetyl-4"-deoxy-4"-oxo-9a-aza-9a-homoerythromycin A in 50 ml of methanol was stored at room temperature for 20 hours, and then the solvent was removed by evaporation in vacuo. This afforded 0.74 g of the desired deacetylated material.

The $^1$H-NMR spectrum of the product showed absorptions at 2.30 (singlet, 6H), 2.38 (singlet, 3H) and 3.35 (singlet, 3H) ppm.

B.
9-Deoxo-9a-methyl-4"-deoxy-4"-beta-amino-9a-aza-9a-homoerythromycin A

A solution of 0.50 g (0.67 mmole) of 9-deoxo-9a-methyl-4"-deoxy-4"-oxo-9a-aza-9a-homoerythromycin A and 0.54 g (6.7 mmole) of ammonium acetate in 50 ml of methanol was prepared, and then acetic acid (7 drops) was added with stirring to adjust the pH to 6. Stirring was continued for 1 hour, and then 0.13 g (2.1 mmole) of sodium cyanoborohydride was added portionwise. Stirring was continued an additional 2.5 hours, and then the reaction mixture was evaporated in vacuo. The residue was partitioned between chloroform and water and the pH of the water layer was adjusted to 2. The aqueous layer was removed and the pH was adjusted to 6.2. The aqueous layer was extracted at pH 6.2 to remove the 4''-hydroxy products and the extracts were discarded. The pH of the aqueous layer was then raised to 9.5 and the aqueous layer was then further extracted with chloroform. The latter extracts were dried and evaporated in vacuo. The residue was redissolved in water at pH 2. The aqueous solution thus obtained was extracted with chloroform at pH 2, pH 6.2 and pH 9.5. The chloroform solution from the extraction at pH 9.5 was dried, evaporated and again dissolved in water at pH 2. This latter aqueous solution was extracted with chloroform at pH 2, pH 6.2 and pH 9.5. The chloroform solution from the extraction at pH 9.5 was dried and evaporated in vacuo to give 0.18 g of a 1:1 mixture of 9-deoxo-9a-methyl-4''-deoxy-4''-beta-amino-9a-aza-9a-homoerythromycin A and its 4''-alpha-epimer.

EXAMPLE 7

9-Deoxo-9a-methyl-2'-O-acetyl-4''-deoxy-4''-oxo-9a-aza-9a-homoerythromycin A

A.

9-Deoxo-9a-methyl-2'-O-acetyl-9a-aza-9a-homoerythromycin A

A solution was prepared from 1.0 g (1.3 mmole) of 9-deoxo-9a-methyl-9a-aza-9a-homoerythromycin A, and 0.13 ml (1.4 mmole) of acetic anhydride in 15 ml of chloroform was stirred for several hours at room temperature. To the solution was added an excess of water and stirring was continued for 30 minutes with the pH being held at 9. The organic phase was then removed, dried and evaporated to give 1.0 g of the desired 2'-O-acetyl compound.

B.

9-Deoxo-9a-methyl-2'-O-acetyl-4''-deoxy-4''-oxo-9a-aza-9a-homoerythromycin A

A mixture was prepared from 7.5 g (9.5 mmole) of 9-deoxy-9a-methyl-2'-O-acetyl-9a-aza-9a-homoerythromycin A, 5.5 g (28 mmole) of N-ethyl-N'-(N,N-diemthylaminopropyl)carbodiimide and 6.7 ml (95 mmole) of dimethyl sulfoxide in 75 ml of dichloromethane. To this mixture was then added, dropwise, with stirring, during 3 minutes, 5.5 g (28 mmole) of pyridinium trifluoroacetate. The temperature rose to 39° C. and then returned to room temperature. Stirring was continued for 2 hours and then an excess of water was added and the pH of the aqueous layer was adjusted to 9. The organic layer was removed, dried and evaporated in vacuo to give 7.5 g of 9-deoxo-9a-methyl-2'-O-acetyl-4''-deoxy-4''-oxo-9a-aza-9a-homoerythromycin A.

The $^1$H-NMR spectrum of the product showed absorptions at 2.05 (singlet, 3H), 2.26 (singlet, 6H), 2.33 (singlet, 3H) and 3.33 (singlet, 3H) ppm.

EXAMPLE 8

9-Deoxo-9a-methyl-2'-O-propionyl-4''-deoxy-4''-oxo-9a-aza-9a-homoerythromycin A

The title compound can be prepared by repeating Example 7, but replacing the acetic anhydride used in Part A by an equimolar amount of propionic anhydride.

EXAMPLE 9

9-Deoxo-4''-deoxy-4''-beta-(4-methoxybenzamido)-9a-aza-9a-homoerythromycin A

To a stirred solution of 730 mg (1 mmole) of 9-deoxo-4''-deoxy-4''-beta-amino-9a-aza-9a-homoerythromycin A in 15 ml of dichloromethane was added 0.20 ml (ca. 2 mmole) of triethylamine, followed by the dropwise addition of a solution of 0.17 ml (ca. 1 mmole) of 4-methoxybenzoyl chloride in 5 ml of dichloromethane, with stirring, at room temperature. Stirring was continued at room temperature for 30 minutes. To the reaction mixture was then added chloroform and water, and the pH was adjusted to 4.5. The layers were separated and the organic layer was discarded. The pH of the aqueous phase was raised to 7.5, and then the aqueous phase was extracted with chloroform. The extract was dried and evaporated in vacuo to give 610 mg (70% yield) of the title product.

The $^1$H-NMR spectrum of the product showed absorptions at 2.25 (singlet, 6H), 3.35 (singlet, 3H), 3.85 (singlet, 3H), 6.95 (doublet, 2H, J=5 Hz) and 7.85 (doublet, 2H, J=5 Hz) ppm.

EXAMPLE 10

Acylation of 9-deoxo-4''-deoxy-4''-beta-amino-9a-aza-9a-homoerythromycin A with the appropriate carboxylic acid chloride of the formula $R^5$-CO-Cl or sulfonyl chloride of the formula $R^6$—$SO_2$—Cl, substantially according to the procedure of Example 9, afforded the following compounds:

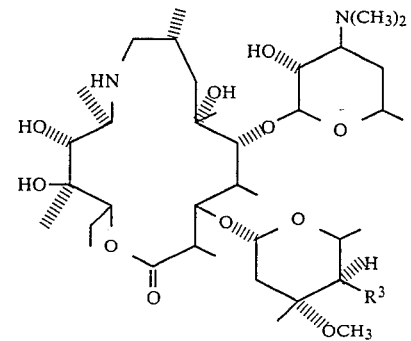

| $R^3$ | Reaction Time (hours) | Reaction Temp. (°C.)* | Yield (%) | $^1$H—NMR (ppm) |
|---|---|---|---|---|
| 2-phenylacetamido | 0.75 | 5 | 94 | |
| benzenesulfonamide | 72 | RT | 38 | |
| 4-chlorobenzene-sulfonamide | 72 | RT | 53 | |
| 4-iodobenzene-sulfonamide | 72 | RT | 63 | |
| octanamido | 0.1 | RT | 74 | |
| 3,3-dimethylbutan-amido | 1.5 | RT | 47 | 2.25 (s, 6H), 3.30 (s, 3H) |
| 3-fluorobenzamido | 1.5 | RT | 43 | 2.25 (s, 6H), 3.40 (s, 3H) |
| 2-trifluoromethyl-benzamido | 0.1 | RT | 65 | 2.20 (s, 6H), 3.30 (s, 3H) 7.40 (bs, 4H) |
| 2-thiophenesulfon-amido | 16 | RT | 56 | 2.25 (s, 6H), 3.35 (s, 3H), 7.05 (m, 1H), 7.45 (m, 2H) |
| 2-furancarboxamido | 1.0 | RT | 64 | 2.25 (s, 6H), 3.35 (s, 3H), 6.60 (m, 2H), 7.10 (d, 1H) |

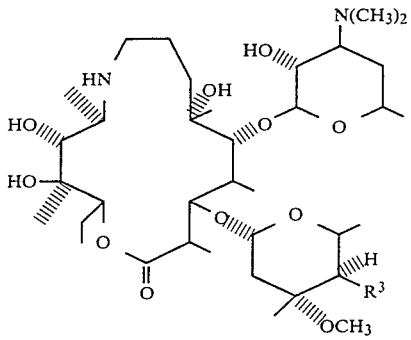

| R³ | Reaction Time (hours) | Reaction Temp. (°C.)* | Yield (%) | ¹H—NMR (ppm) |
|---|---|---|---|---|
| 3-phenylpropion-amido | 0.25 | RT | 42 | 7.40 (s, 1H) 2.30 (s, 6H), 3.25 (s, 3H), 7.15 (s, 5H) |
| 2-chlorobenzamido | 0.25 | RT | 70 | 2.30 (s, 6H), 3.30 (s, 3H), 7.35 (m, 4H) |
| 2-fluorobenzamido | 0.25 | RT | 66 | 2.30 (s, 6H), 3.40 (s, 3H), 7.20 (m, 4H) |
| 2,2-dimethylpropion-amido | 0.1 | RT | 98 | 2.25 (s, 6H), 3.35 (s, 3H) |
| 2-(4-chlorophen-oxy)acetamido | 0.25 | RT | 63 | 2.25 (s, 6H), 3.30 (s, 3H), 6.60–7.35 (m, 6H) |
| 3-chlorobenzamido | 0.25 | RT | 65 | 2.30 (s, 6H), 3.30 (s, 3H), 7.40–7.90 (m, 4H) |
| 2-phenoxyacetamido | 0.25 | RT | 78 | 2.30 (s, 6H), 3.30 (s, 3H), 6.70–7.40 (m, 7H) |
| 4-fluorobenzoyl | 0.1 | RT | 69 | 2.30 (s, 6H), 3.35 (s, 3H), 6.95–7.30 (m), 7.70–8.10 (m) |
| 2-pyrazinecarbox-amido | 0.5 | RT | 82 | 2.30 (s, 6H), 3.40 (s, 3H), 7.60 (s, 3H) |
| 2-(4-nitrophenoxy)-acetamido | 16 | RT | 41 | |

*"RT" indicates room temperature

EXAMPLE 11

Acylation of 9-deoxo-4″-deoxy-4″-alpha-amino-9a-aza-9a-homoerythromycin A with benzyl chloroformate (reaction time 0.75 hours) and with benzenesulfonyl chloride (reaction time 16 hours), substantially according to the procedure of Example 9, afforded the following compounds:
9-deoxo-4″-deoxy-4″-alpha-benzyloxycarbonylamino-9a-aza-9a-homoerythromycin A (84% yield) and
9-deoxo-4″-deoxy-4″-alpha-benzenesulfonamido-9a-aza-9a-homoerythromycin A (24% yield), respectively.

EXAMPLE 12

By acylation of 9-deoxo-4″-deoxy-4″-beta-amino-9a-aza-9a-homoerythromycin A with the appropriate acid chloride of the formula R⁵—CO—Cl or sulfonyl chloride of the formula R⁶—SO₂—Cl, using the procedure of Example 9, following compounds can be prepared.

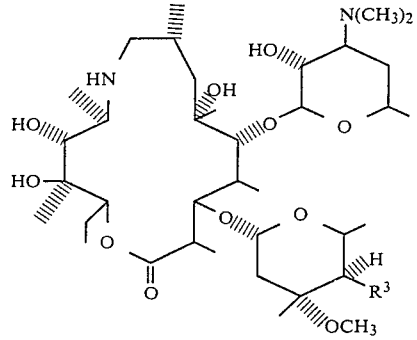

| R³ |
|---|
| acetamido |
| heptanamido |
| 2-(2-thienyl)acetamido |
| 2-pyrimidine carboxamido |
| benzamido |
| 4-phenylbutanamido |
| 2-(3-bromophenyl)acetamido |
| 3-(3-methylphenyl)propionamido |
| 2-(4-isopropylphenyl)acetamido |
| 2-(4-propoxyphenyl)acetamido |
| 2-(2-fluorophenoxy)acetamido |
| 2-(3-bromophenoxy)acetamido |
| 3-fluorobenzyloxycarbonylamino |
| 4-chlorobenzyloxycarbonylamino |
| 4-bromobenzyloxycarbonylamino |
| 3-thiophenesulfonamido |
| 3-bromobenzenesulfonamido |

EXAMPLE 13

By acylation of 9-deoxo-4″-deoxy-4″-alpha-amino-9a-aza-9a-homoerythromycin A with the appropriate acid chloride of the formula R⁵—CO—Cl or sulfonyl chloride of the formula R⁶—SO₂—Cl, using the procedure of Example 9, the following compounds can be prepared.

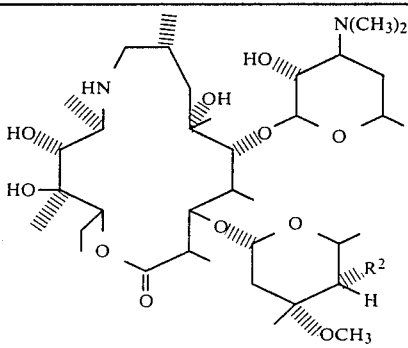

| R² |
|---|
| propionamido |
| 2-(2-thienyl)acetamido |
| benzamido |
| 4-chlorobenzamido |
| 2-phenylpropionamido |
| 2-phenoxyacetamido |
| 2-(3-chlorophenoxy)acetamido |
| 2-furansulfonamido |
| 3-chlorobenzenesulfonamido |
| 4-bromobenzenesulfonamido |

EXAMPLE 14

9-Deoxo-4''-deoxy-4''-beta-(2-[4-methoxyphenyl]acetamido)-9a-aza-9a-homoerythromycin A To 50 ml of dichloromethane was added 730 mg (1 mmole) of 9-deoxo-4''-deoxy-4''-beta-amino-9a-aza-9a-homoerythromycin A, 500 mg (3 mmole) of 2-(4-methoxyphenyl)acetic acid and 800 mg (4 mmole) of dicyclohexylcarbodiimide, and the reaction mixture was stirred at room temperature for 2 hours. Water was then added to the reaction mixture, and the pH of the aqueous layer was adjusted to 4. The layers were separated and the aqueous layer was further extracted with chloroform at pH 4. The dichloromethane layer and chloroform extracts were discarded. The pH of the aqueous layer was raised to 6.5, and it was then extracted three times with chloroform. The latter extracts were dried and evaporated in vacuo to give 650 mg (74% yield) of the title compound.

The $^1$H-NMR spectrum of the product showed absorptions at 2.25 (singlet, 6H), 3.25 (singlet, 3H), 3.75 (singlet, 3H), 6.90 (doublet, 2H, J=5 Hz) and 7.15 (doublet, 2H, J=5 Hz) ppm.

EXAMPLE 15

Reaction of 9-deoxo-4''-deoxy-4''-beta-amino-9a-aza-9a-homoerythromycin A with the appropriate acid of the formula $R^5$—$CO_2$—H, substantially according to the procedure of Example 14, afforded the compounds tabulated below. In some instances it was necessary to add additional acid of the formula $R^5$—$CO_2$—H and additional carbodiimide during the course of the reaction to ensure complete acylation of the macrolide compound.

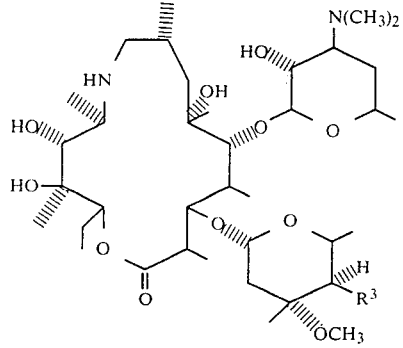

| $R^3$ | Reaction Time (hours) | Yield (%) | $^1$H—NMR (ppm) |
|---|---|---|---|
| 2-(4-fluorophenyl)-acetamido | 18 | 57 | 2.30 (s, 6H), 3.40 (s, 3H), 6.90-7.50 (m, 4H) |
| 4-phenylbutanamido | 2 | 71 | 2.30 (s, 6H), 3.30 (s, 3H), 7.20 (s, 5H) |
| 2-pyridinecarboxamido | 4 | 67 | 2.30 (s, 6H), 3.40 (s, 3H), 7.40-8.40 (m, 4H) |
| 2-(3-thienyl)-acetamido | 0.5 | 34 | 2.25 (s, 6H), 3.30 (s, 3H), 6.90-7.40 (m, 3H) |
| 2-(2-fluorophenyl)-acetamido | 4 | 41 | 2.30 (m, 6H), 3.30 (s, 3H), 6.90-7.40 (m, 4H) |
| 3-isoxazole-carboxamido | 72 | 52 | |
| 2-(2-chlorophenyl)-acetamido | 5 | 25 | 2.25 (s, 6H), 3.30 (s, 3H), 7.25 (m, 4H) |
| 2-(3-fluorophenyl)-acetamido | 72 | 40 | 2.25 (s, 6H), 3.30 (s, 3H), 6.90-7.30 (m, 4H) |
| 2-(3-chlorophenyl)-acetamido | 18 | 48 | 2.30 (s, 6H), 3.30 (s, 3H), 7.20-7.40 (m, 4H) |
| 2-(4-chlorophenyl)-acetamido | 120 | 45 | 2.30 (s, 6H), 7.30 (s, 4H) |

EXAMPLE 16

9-Deoxo-4''-deoxy-4''-beta-(2-[4-hydroxyphenyl]acetamido)-9a-aza-9a-homoerythromycin A A stirred solution of 120 mg (0.82 mmole) of 2-(4-hydroxyphenyl)acetic acid and 0.15 ml (1.8 mmole) of N-methylmorpholine in 30 ml of dichloromethane was cooled to −15° C., and then 0.18 ml (1.3 mmole) of isobutyl chloroformate was added. The resulting mixture was stirred at −15° to −10° C. for 30 minutes, and then a solution of 600 mg (0.82 mmole) of 9-deoxo-4''-deoxy-4''-beta-amino-9a-aza-9a-homoerythromycin A in 10 ml of dichloromethane was added. Stirring was continued for 30 minutes at −10° C., for 30 minutes at −5° C. and for 30 minutes at 0° C. Water was then added to the reaction mixture and the pH of the aqueous layer was adjusted to 4. The layers were separated and the aqueous layer was further extracted with chloroform at pH 4. The dichloromethane layer and the chloroform extracts were discarded. The pH of the aqueous layer was raised to 6.5, and it was then extracted three times with chloroform. The latter extracts were combined, dried and evaporated in vacuo to give 470 mg (66% yield) of the title compound.

EXAMPLE 17

9-Deoxo-4''-deoxy-4''-beta-(2-[4-aminophenyl]acetamido)-9a-aza-9a-homoerythromycin A The title compound was prepared in 40% yield by reaction of 9-deoxo-4''-deoxy-4''-beta-amino-9a-aza-9a-homoerythromycin A with the mixed anhydride prepared from 2-(4-aminophenyl)acetic acid and isobutyl chloroformate, using the procedure of Example 16.

The $^1$H-NMR spectrum of the product showed absorptions at 2.25 (singlet, 6H) and 7.15 (singlet, 4H) ppm.

EXAMPLE 18

9-Deoxo-9a-methyl-4''-deoxy-4''-beta-(4-chlorobenzenesulfonamido)-9a-aza-9a-homoerythromycin A A mixture prepared from 200 mg (0.22 mmole) of 9-deoxo-4''-deoxy-4''-beta-(4-chlorobenzenesulfonamido)-9a-aza-9a-homoerythromycin A, 0.03 ml of 37% aqueous formaldehyde, 0.011 of 98% formic acid and 10 ml of chloroform was heated under reflux for 16 hours. The reaction mixture was cooled, and water was added. The pH of the aqueous phase was adjusted to 9.6 and the layers were separated. The organic layer was washed with water, dried and evaporated in vacuo to give 200 mg (94% yield) of the title product.

The $^1$H-NMR spectrum of the product showed absorptions at 2.25 (s, 6H), 3.30 (s, 3H), 7.35 (doublet, 2H, J=5 Hz) and 7.80 (doublet, 2H, J=5 Hz) ppm.

EXAMPLE 19

Methylation of the appropriate 9-deoxo-4''-deoxy-4''-beta-(acylamino)-9a-aza-9a-homoerythromycin A compound with formaldehyde and formic acid, substantially according to the procedure of Example 18, afforded the following compounds:

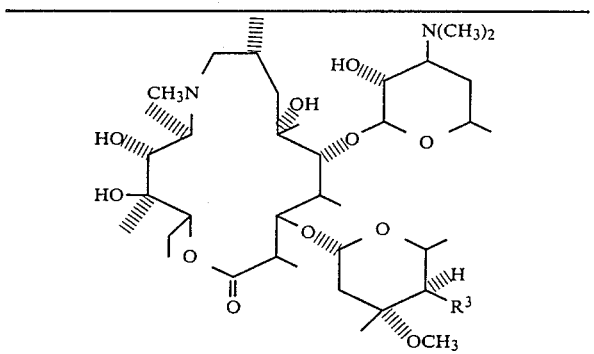

| $R^3$ | Reaction Time (hours) | Yield (%) | $^1$H—NMR (ppm) |
|---|---|---|---|
| 4-iodobenzene-sulfonamido | 4.5 | 92 | 2.40 (s, 9H), 3.23 (s, 3H), 7.50 (d, 2H), 7.85 (d, 2H) |
| 3-fluorobenzamido | 1.5 | 52 | 2.30 (s, 9H), 3.35 (s, 3H), 7.00–7.70 (m, 4H) |
| 3,3-dimethylbutan-amido | 2 | 62 | 2.30 (s, 9H), 3.30 (s, 3H) |
| octanamido | 4 | 93 | |
| 2-(4-fluorophenyl)-acetamido | 4 | 74 | 2.35 (s, 9H), 3.20 (s, 3H), 6.90–7.25 (m, 4H) |
| 2-(2-trifluoromethyl-phenyl)acetamido | 4 | 98 | 2.30 (s, 9H), 3.30 (s, 3H), 7.30–7.70 (m, 4H) |
| 4-methoxybenz-amido | 3 | 91 | |
| 2-thiophene-sulfonamido | 16 | 96 | 2.30 (s, 9H), 3.35 (s, 3H), 6.95–7.15 (m, 1H), 7.45–7.65 (m, 2H) |
| 2-furancarboxamido | 2 | 87 | 2.30 (s, 9H), 3.40 (s, 3H), 6.40–6.75 (m, 2H), 7.10 (m, 1H), 7.50 (m, 1H) |
| 3-phenylpropion-amido | 16 | 76 | 2.30 (s, 9H), 3.25 (s, 3H), 7.20 (s, 5H) |
| 2-chlorobenzamido | 3 | 93 | 2.25 (s, 9H), 3.30 (s, 3H), 7.35 (m, 4H) |
| 2-fluorobenzamido | 2.5 | 96 | 2.30 (s, 9H), 3.30 (s, 3H), 6.65–7.45 and 7.70–8.20 (m, 4H) |
| 2-phenylacetamido | 16 | 69 | 2.25 (s, 9H), 3.25 (s, 3H), 7.20 (s, 5H) |
| 2,2-dimethyl-propionamido | 3.5 | 95 | 2.30 (s, 9H), 3.30 (s, 3H) |
| 3-chlorobenzamido | 3 | 91 | 2.30 (s, 9H), 3.30 (s, 3H), 7.30–7.80 (m, 4H) |
| 2-(4-chlorophen-oxy)acetamido | 2.5 | 70 | 2.30 (s, 9H), 3.35 (s, 3H), 6.60–7.40 (m, 6H) |
| 2-phenoxyacetamido | 3 | 72 | 2.30 (s, 9H), 3.30 (s, 3H), 6.80–7.40 (m, 5H) |
| 4-fluorobenzamido | 2.5 | 61 | 2.30 (s, 9H), 3.35 (s, 3H), 7.00–7.30 (m, 2H), 7.85–8.00 (m, 2H) |
| 2-pyrazinecar-boxamido | 2 | 93 | 2.30 (s, 9H), 3.35 (s, 3H), 8.60–8.95 (m, 3H) |
| 2-(4-methoxy-phenyl)acetamido | 2.5 | 96 | 2.25 (s, 9H), 3.35 (s, 3H), 3.80 (s, 3H), 6.90 (d, 2H), 7.25 (d, 2H) |
| 2-pyridine carboxamido | 2.5 | 98 | 2.35 (s, 9H), 3.35 (s, 3H), 7.40–8.90 (m, 4H) |
| 4-phenylbutanamido | 3 | 92 | 2.30 (s, 9H), 3.35 (s, 3H), 7.15 (s, 5H) |
| 2-(3-thienyl)-acetamido | 2 | 86 | 2.25 (s, 9H), 3.30 (s, 3H), 6.80–7.30 (m, 3H) |
| 2-(2-fluorophenyl)-acetamido | 2.5 | 94 | |
| 3-isoxazolecar-boxamido | 2.5 | 69 | 2.25 (s, 9H), 3.40 (s, 3H), 6.65–7.10 (m, 2H) |
| 2-(3-fluorophenyl)-acetamido | 3.5 | 87 | 2.30 (s, 9H), 3.35 (s, 3H), 6.80–7.10 (m, 4H) |
| 2-(2-chlorophenyl)-acetamido | 3 | 94 | |
| 2-(3-chlorophenyl)-acetamido | 3 | 95 | 2.25 (s, 9H), 3.35 (s, 3H), 7.20 (m, 4H) |
| 2-(4-chlorophenyl)-acetamido | 4 | 89 | 2.25 (s, 9H), 3.30 (s, 3H), 7.20 (s, 4H) |
| 2-(4-hydroxy-phenyl)acetamido | 4 | 91 | 2.30 (s, 9H), 6.95–7.40 (m, 4H) |
| 2-(4-nitrophenyl)-acetamido | 2.5 | 94 | 2.30 (s, 9H), 3.30 (s, 3H), 7.40 (d, 2H), 8.10 (d, 2H) |
| benzenesulfonamido | 16 | 75 | |

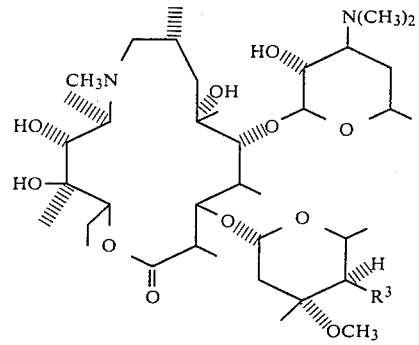

EXAMPLE 20

Methylation of 9-deoxo-4''-deoxy-4''-alpha-benzyloxycarbonylamino-9a-aza-9a-homoerythromycin A and 9-deoxo-4''-deoxy-4''-alpha-benzenesulfonamido-9a-aza-9a-homoerythromycin A with formaldehyde and formic acid, substantially according to the procedure of Example 18, afforded the following compounds:

9-deoxo-9a-methyl-4''-deoxy-4''-alpha-benzyloxycarbonylamino-9a-aza-9a-homoerythromycin A (100% yield) and 9-deoxo-9a-methyl-4''-deoxy-4''-alpha-benzenesulfonamido-9a-aza-9a-homoerythromycin A (70% yield), respectively.

EXAMPLE 21

By methylation of the appropriate 9-deoxo-4''-deoxy-4''-beta-acylamino-9a-aza-9a-homoerythromycin A from Example 12 with formaldehyde and formic acid, using the procedure of Example 18, the following compounds can be prepared:

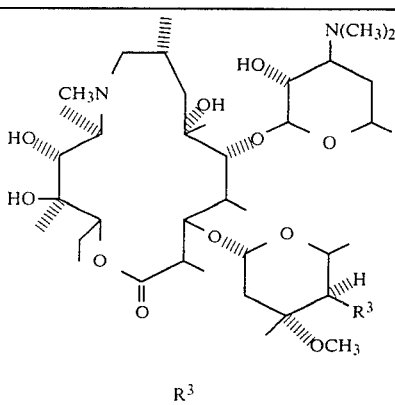

| $R^3$ |
|---|
| acetamido |
| heptanamido |
| 2-(2-thienyl)acetamido |
| 2-pyrimidine carboxamido |
| benzamido |
| 4-phenylbutanamido |
| 2-(3-bromophenyl)acetamido |
| 3-(3-methylphenyl)propionamido |
| 2-(4-isopropylphenyl)acetamido |
| 2-(4-propoxyphenyl)acetamido |
| 2-(2-fluorophenoxy)acetamido |
| 2-(3-bromophenoxy)acetamido |
| 3-fluorobenzyloxycarbonylamino |
| 4-chlorobenzyloxycarbonylamino |
| 4-bromobenzyloxycarbonylamino |
| 3-thiophenesulfonamido |
| 3-bromobenzenesulfonamido |

EXAMPLE 22

By methylation of the appropriate 9-deoxo-4''-deoxy-4''-alpha-acylamino-9a-aza-9a-homoerythromycin A from Example 13 with formaldehyde and formic acid, using the procedure of Example 18, the following compounds can be prepared:

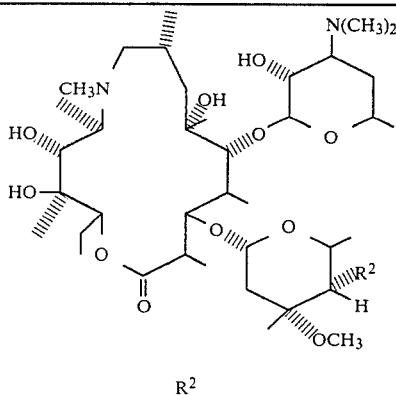

| $R^2$ |
|---|
| propionamido |
| 2-(2-thienyl)acetamido |
| benzamido |
| 4-chlorobenzamido |
| 2-phenylpropionamido |
| 2-phenoxyacetamido |
| 2-(3-chlorophenoxy)acetamido |
| 2-furansulfonamido |
| 3-chlorobenzenesulfonamido |
| 4-bromobenzenesulfonamido |

PREPARATION 1

4''-Deoxy-4''-alpha-amino-erythromycin A

A mixture of 10.0 g (13.6 mmole) of 4''-deoxy-4''-oxo-erythromycin A, 10.5 g of ammonium acetate and 10.0 of Raney nickel in 150 ml of methanol was shaken under an atmosphere of hydrogen, at an initial hydrogen pressure of ca. 4 kg/cm$^2$, at room temperature, overnight. An additional 10.5 g of ammonium acetate and 10.0 g of Raney nickel were then added and the mixture was again shaken under hydrogen, at initial hydrogen pressure of ca. 4 kg/cm$^2$, at room temperature, overnight. The catalyst was removed by filtration and the filtrate was concentrated in vacuo to ca. 50 ml. The concentrated filtrate was then poured with stirring into a mixture of 250 ml of water and 200 ml of chloroform, and the pH of the aqueous layer was adjusted to 5.4. The organic layer was removed and discarded and the aqueous layer was further extracted with chloroform at pH 5.4. The further extracts were discarded. The pH of the aqueous phase was adjusted to 9.6 and then the aqueous phase was extracted with chloroform. The latter extracts were dried (Na$_2$SO$_4$) and then concentrated in vacuo to give 5.74 g of a white foam. The foam was dissolved in 35 ml of hot isopropanol, and the solution was allowed to cool to room temperature with stirring. The solid which had formed was recovered by filtration and dried, to afford 3.54 g of 4''-deoxy-4''-alpha-amino-erythromycin A, contaminated with 5–10% of its 4''-epimer.

The proportion of 4''-beta-amino epimer can be reduced by successive recrystallizations from isopropanol.

PREPARATION 2

4''-Deoxy-4''-beta-amino-erythromycin A

Twenty grams of 4''-deoxy-4''-oxo-erythromycin A, 31.6 g ammonium acetate and 10 g of 10% palladium-on-carbon in 200 ml of methanol was shaken at ambient temperatures in a hydrogen atmosphere at an initial pressure of ca. 4 kg/cm$^2$ overnight. The spent catalyst was filtered and the filtrate concentrated to dryness in vacuo. The residue was partitioned between water-chloroform at a pH of 5.5. The aqueous layer was separated, the pH adjusted to 9.6 and chloroform added. The organic layer was separated, dried over sodium sulfate and concentrated under reduced pressure to dryness. The residual white foam (19 g) was triturated with 150 ml of diethyl ether at room temperature for 30 minutes. The resulting solids were filtered and dried to give 9.45 g of 4''-deoxy-4''-beta-amino-erythromycin A.

We claim:

1. A macrolide antibiotic compound of the formula

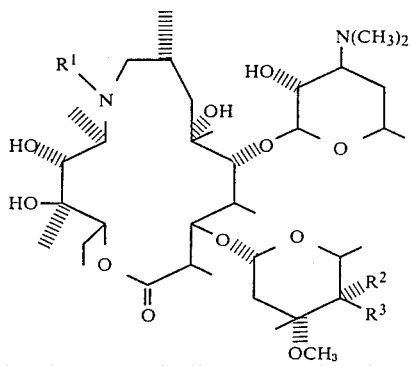

and the pharmaceutically-acceptable acid-addition salts thereof; wherein $R^1$ is selected from the group consisting of hydrogen and methyl; and $R^2$ and $R^3$ are each selected from the group consisting of hydrogen, NH—CO—$R^5$ and NH—SO$_2$—$R^6$; provided that one of $R^2$ and $R^3$ is always hydrogen, but $R^2$ and $R^3$ are not both hydrogen;

wherein:

(i) $R^5$ is selected from the group consisting of

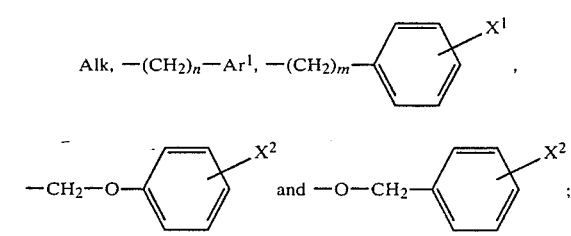

wherein Alk is alkyl having from 1 to 8 carbons; Ar$^1$ is thienyl, furyl, isoxazolyl, pyridyl, pyrazinyl or pyrimidyl; $X^1$ is hydrogen, fluoro, chloro, bromo, hydroxy, amino, nitro, trifluoromethyl, alkyl having 1 to 3 carbons or alkoxy having 1 to 3 carbons; $X^2$ is hydrogen, fluoro, chloro or bromo; n is 0 or 1; and m is 0, 1, 2 or 3; and (ii) $R^6$ is selected from the group consisting of

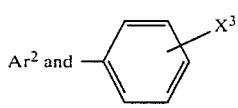

wherein Ar$^2$ is thienyl or furyl and $X^3$ is hydrogen, chloro, bromo or iodo.

2. A compound according to claim 1, wherein $R^2$ is hydrogen and $R^3$ is said NH—CO—$R^5$.

3. A compound according to claim 2, wherein $R^1$ is methyl.

4. A compound according to claim 3, wherein $R^5$ is said alkyl.

5. The compound according to claim 4, wherein said alkyl is n-heptyl.

6. A compound according to claim 3, wherein $R^5$ is said

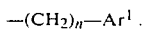

7. The compound according to claim 6, wherein Ar$^1$ is 3-thienyl and n is 2.

8. A compound according to claim 3, wherein $R^5$ is said

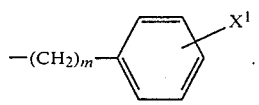

9. A compound according to claim 8, wherein m is 1.

10. A compound according to claim 9, wherein $X^1$ is fluoro, hydroxy or said alkoxy.

11. The compound according to claim 10, wherein $X^1$ is 4-fluoro.

12. The compound according to claim 10, wherein $X^1$ is 4-hydroxy.

13. The compound according to claim 10, wherein $X^1$ is 4-methoxy.

14. A compound according to claim 3, wherein $R^5$ is said

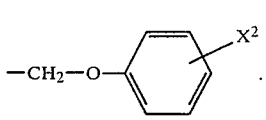

15. The compound according to claim 14, wherein $X^2$ is 4-chloro.

16. A compound according to claim 3, wherein $R^5$ is said

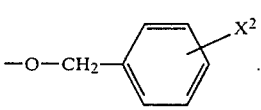

17. The compound according to claim 16, wherein $X^2$ is hydrogen.

18. A compound according to claim 1, wherein $R^2$ is hydrogen and $R^3$ is said NH—SO$_2$—$R^6$.

19. A compound according to claim 18, wherein $R^1$ is methyl.

20. A compound according to claim 19, wherein $R^6$ is said

21. The compound according to claim 20, wherein $X^3$ is 4-chloro.

22. A method of treating a bacterial infection in a mammalian subject, which comprises administering thereto an antibacterially effective amount of a macrolide antibiotic compound of the formula

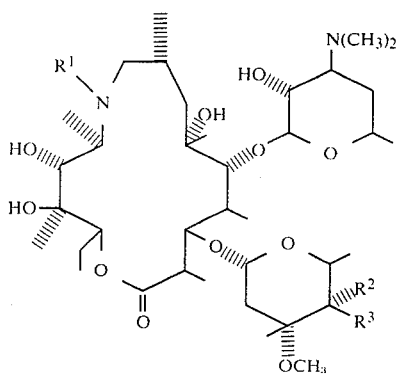

or a pharmaceutically-acceptable acid-addition salt thereof; wherein $R^1$ is selected from the group consisting of hydrogen and methyl; and $R^2$ and $R^3$ are each selected from the group consisting of hydrogen, NH—CO—$R^5$ and NH—SO$_2$—$R^6$;

provided that one of $R^2$ and $R^3$ is always hydrogen, but $R^2$ and $R^3$ are not both hydrogen;

wherein:

(i) $R^5$ is selected from the group consisting of

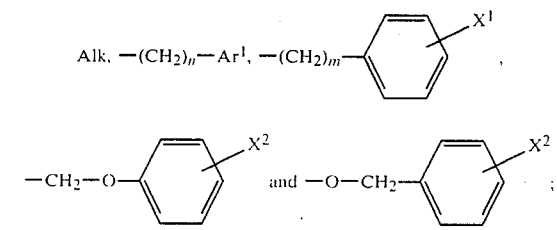

wherein Alk is alkyl having from 1 to 8 carbons; $Ar^1$ is thienyl, furyl, isoxazolyl, pyridyl, pyrazinyl or pyrimidyl; $X^1$ is hydrogen, fluoro, chloro, bromo, hydroxy, amino, nitro, trifluoromethyl, alkyl having 1 to 3 carbons or alkoxy having 1 to 3 carbons; $X^2$ is hydrogen, fluoro, chloro or bromo; n is 0 or 1; and m is 0, 1, 2 or 3; and (ii) $R^6$ is selected from the group consisting of

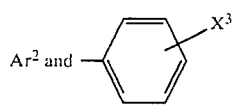

wherein $Ar^2$ is thienyl or furyl and $X^3$ is hydrogen, chloro, bromo, or iodo.

23. A pharmaceutical composition which comprises a pharmaceutically-acceptable carrier and a macrolide antibiotic compound according to claim 1, wherein the weight ratio of the pharmaceutically-acceptable carrier to the macrolide antibiotic compound is in the range from 4:1 to 1:4.

* * * * *